US007652204B2

(12) United States Patent  
Elias

(10) Patent No.: US 7,652,204 B2  
(45) Date of Patent: Jan. 26, 2010

(54) **BREEDING OF *FUSARIUM* RESISTANT TETRAPLOID *DURUM* WHEAT**

(75) Inventor: Elias M Elias, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 323 days.

(21) Appl. No.: 11/071,272

(22) Filed: Mar. 2, 2005

(65) Prior Publication Data

US 2005/0273875 A1    Dec. 8, 2005

Related U.S. Application Data

(60) Provisional application No. 60/577,854, filed on Jun. 8, 2004.

(51) Int. Cl.
*A01H 1/00* (2006.01)
*A01H 1/02* (2006.01)
*A01H 5/00* (2006.01)
*A23L 1/00* (2006.01)

(52) U.S. Cl. .................... 800/320.3; 800/265; 800/298; 800/260

(58) Field of Classification Search ........................ None
See application file for complete search history.

(56) References Cited

U.S. PATENT DOCUMENTS

| | | | |
|---|---|---|---|
| 4,143,486 A | 3/1979 | Maan | |
| 4,406,086 A | 9/1983 | Hayward | |
| 5,498,829 A | 3/1996 | Goertzen et al. | |
| 5,859,315 A | 1/1999 | Payne | |
| 6,448,476 B1 | 9/2002 | Barry | |
| 6,818,813 B1 * | 11/2004 | Edge et al. | 800/320.3 |
| 6,921,852 B2 * | 7/2005 | Lively et al. | 800/320.3 |

OTHER PUBLICATIONS

Chen et al. Plant Breeding (2001), vol. 120, pp. 375-380.*
Jauhar et al. Euphytica (2001), vol. 118:127-136.*
Stack et al. Crop Science 42:637-642 (2002).*
Cantrell, "Breeding and Genetics of Durum Wheat," in *Plant Breeding Reviews vol. 5* (Janick, Ed.), Avi Publishing Co., 1987, pp. 11-40.
Knott, "Transferring alien genes to wheat," in *Wheat and Wheat Improvement*, 2nd Ed. (Heyne, ed.), American Society of Agronomy, Madison, WI 1987, pp. 462-471.
"Report of The 2003 Uniform Regional Scab Nursery for Spring Wheat Parents" datasheet [online]. U.S. Wheat and Barley Scab Initiative [retrieved on May 25, 2006]. Retrieved from the Internet:<http://www.scabusa.org/pdfs_dbupload/03_URSN_FHB_Report.pdf>; 14 pgs.
Suresh et al., "Efficiency and Efficacy of Marker Assisted Selection Over Phenotypic Selection for FHB Resistance in *Durum* Wheat" 2002 National *Fusarium* Head Blight Forum Proceedings, U.S. Wheat and Barley Scab Initiative [online]. Erlanger, KY Dec. 7, 2002 to Dec. 9, 2002, avaliable online [retrieved May 25, 2006]. Retrieved from the Internet:<http://www.scabusa.org/pdfs/forum_02_proc.pdf>; Title page, Publication page, Table of Contents, and 1 pg abstract (14 pgs. total).
Anderson et al., "DNA markers for *Fusarium* head blight resistance QTLs in two wheat populations" *Theor. Appl. Genet.*, Jun. 2001;102(8):1164-1168.
Bhamidimarri et al., "Comparisons of Marker Assisted Selection to Phenotypic Selection for FHB Resistance in *Durum* Wheat," in *Agronomy Abstracts*, Annual Meetings Abstracst, Nov. 2-6, 2003, Denver Colorado, American Society of Agronomy, Madison, WI 2003, C01-bhamidimarri795209-oral (1 page abstract).
Cai et al., "Identification of a 1B/1R wheat-rye chromosome translocation". *Theor. Appl. Genet.*, Jan. 1989; 77(1):81-83.
Cantrell et al., "Registration of 'Renville' *Durum* Wheat" *Crop Sci.*, 1989;29:1329-1330.
Cantrell et al., "Registration of 'Monroe' *Durum* Wheat" *Crop Sci.*, 1986;26:200-201.
Chee et al., "Evaluation of a high grain protein QTL from *Triticum turgidum* L. var. dicoccoides in an adapted durum wheat background" *Crop Sci.*, Mar. 2001-Apr. 2001; 41(2):295-301.
"Crop Production 2-2" [online]. National Agriculture Statistics Service, Agricultural Statistics Board, U.S. Department of Agriculture, Washington, D.C. Sep 14, 2001 [retrieved on Apr.10, 2006]. Retrieved from the Internet:usda.mannlib.cornell.edu/reports/nassr/field/pcp-bb/2001/crop0901.pdf>; 45 pgs.
Dexter et al., "Effect of *Fusarium* head blight in semolina milling and pasta-making quality of *durum* wheat" *Cereal Chem.*, Sep.-Oct. 1997;74(5):519-525.
Elias, Elias "Identify Sources of Resistance to *Fusarium* Head Blight in *Durum* Wheat," Project Abstract, Grant No. 59-0790-4-098 [online]. U.S. Wheat and Barley Scab Initiative, United Stated Department of Agriculture- Agricultural Research Service, May 2005 to Apr. 2006 [retrieved on Apr. 7, 2006]. Retrieved from the Internet:www.scabusa.org/pdfs_dbupload/FY05_GIR_Elias_Abstract.pdf>; 1 pg.
Elias, Elias "Development of *Durum* Wheat Resistant to *Fusarium* Head Blight," Project Abstract, Grant No. 59-0790-4-098 [online]. U.S. Wheat and Barley Scab Initiative, United Stated Department of Agriculture- Agricultural Research Service, May 2005 to Apr. 2006 [retrieved on Apr. 7, 2006]. Retrieved from the Internet: www.scabusa.org/pdfs_dbupload/FY05_VDUN_Elias_Abstract.pdf>; 1 pg.
Elias, Elias "Identify and Develop *Durum* Wheat Resistant to *Fusarium* Head Blight," Final Performance Report, Grant No. 59-0790-4-098 [online]. U.S. Wheat and Barley Scab Initiative, United Stated Department of Agriculture- Agricultural Research Service, May 2004 to Apr. 2005 [retrieved on Apr. 7, 2006]. Retrieved from the Internet:www.scabusa.org/pdfs_dbupload/FY04_FPR_Elias_Final.pdf>; 4 pgs.

(Continued)

*Primary Examiner*—Medina A Ibrahim
(74) *Attorney, Agent, or Firm*—Mueting Raasch & Gebhardt, P.A.

(57) ABSTRACT

The invention relates to a method of producing *Fusarium* resistant tetraploid wheat by crossing a hexaploid *Fusarium* resistant wheat with a teraploid durum wheat.

12 Claims, 2 Drawing Sheets

OTHER PUBLICATIONS

Elias, Elias "Identify Sources of Resistance to *Fusarium* Head Blight in *Durum* Wheat," Project Abstract, Grant No. 59-0790-9-033 [online]. U.S. Wheat and Barley Scab Initiative, United Stated Department of Agriculture- Agricultural Research Service, May 2004 to Apr. 2005 [retrieved on Apr. 7, 2006]. Retrieved from the Internet:www.scabusa.org/pdfs_dbupload/04Elias_ABSTRACT_GIE.pdf> ; 1 pg.

Elias, Elias "Development of *Durum* Wheat Resistant to *Fusarium* Head Blight," Project Abstract, Grant No. 59-0790-9-033 [online]. U.S. Wheat and Barley Scab Initiative, United Stated Department of Agriculture- Agricultural Research Service, May 2004 to Apr. 2005 [retrieved on Apr. 7, 2006]. Retrieved from the Internet:www.scabusa.org/pdfs_dbupload/04Elias_ABSTRACT_VDUN.pdf>; 1 pg.

Elias, Elias "Identify and Develop *Durum* Wheat Resistant to *Fusarium* Head Blight," Final Performance Report, Grant No. 59-0790-9-033 [online]. U.S. Wheat and Barley Scab Initiative, United Stated Department of Agriculture- Agricultural Research Service, May 2003 to Apr. 2004 [retrieved on Apr. 7, 2006]. Retrieved from the Internet:www.scabusa.org/pdfs_dbupload/FY03_FPR_Elias_Final.pdf>; 4 pgs.

Elias, Elias "Identify Sources of Resistance to *Fusarium* Head Blight in *Durum* Wheat," Project Abstract, Grant No. 59-0790-9-033 [online]. U.S. Wheat and Barley Scab Initiative, United Stated Department of Agriculture- Agricultural Research Service, May 2003 to Apr. 2004 [retrieved on Apr. 7, 2006]. Retrieved from the Internet:/www.scabusa.org/pdfs_dbupload/03Elias_ABSTRACT_GIE.pdf >; 1 pg.

Elias, Elias "Development of *Durum* Wheat Resistant to *Fusarium* Head Blight," Project Abstract, Grant No. 59-0790-9-033 [online]. U.S. Wheat and Barley Scab Initiative, United Stated Department of Agriculture- Agricultural Research Service, May 2003 to Apr. 2004 [retrieved on Apr. 7, 2006]. Retrieved from the Internet:www.scabusa.org/pdfs_dbupload/03Elias_ABSTRACT_VDUN.pdf>; 1 pg.

Elias, Elias "*Fusarium* Head Blight Research," Final Performance Report, Grant No. 59-0790-9-033 [online]. U.S. Wheat and Barley Scab Initiative, United Stated Department of Agriculture- Agricultural Research Service, May 2002 to Apr. 2003 [retrieved on Apr. 7, 2006]. Retrieved from the Internet:www.scabusa.org/pdfs_dbupload/02FPR_Elias_Final.pdf>; 4 pgs.

Elias, Elias "Identify Sources of Resistance to *Fusarium* Head Blight in *Durum* Wheat," Project Abstract, Grant No. 59-0790-9-033 [online]. U.S. Wheat and Barley Scab Initiative, United Stated Department of Agriculture- Agricultural ResearchService, May 2002 to Apr. 2003 [retrieved on Apr.7, 2006]. Retrieved from the Internet:www.scabusa.org/pdfs_dbupload/02_Elias_Abstract_GIE.pdf>; 1 pg.

Elias, Elias "Development of *Durum* Wheat Resistant to *Fusarium* Head Blight," Project Abstract, Grant No. 59-0790-9-033 [online]. U.S. Wheat and Barley Scab Initiative, United Stated Department of Agriculture- Agricultural Research Service, May 2002 to Apr. 2003 [retrieved on Apr 7, 2006]. Retrieved from the Internet:www.scabusa.org/pdfs_dbupload/02_Elias_Abstract_VDUN.pdf >; 1 pg.

Elias, Elias "*Fusarium* Head Blight Research," Final Performance Report, Grant No. 59-0790-9-033 [online]. U.S. Wheat and Barley Scab Initiative, United Stated Department of Agriculture- Agricultural Research Service, May 2001 to Apr. 2002 [retrieved on Apr. 7, 2006]. Retrieved from the Internet:www.scabus a.org/pdfs_dbupload/01_FPR_ Elias-Final.pdf>; 4 pgs.

Elias, Elias "*Fusarium* Head Blight Research," Final Performance Report, Grant No. 59-0790-9-033 [online]. U.S, Wheat and Barley Scab Initiative, United Stated Department of Agriculture- Agricultural Research Service, May 2000 to Apr. 2001 [retrieved on Apr. 7, 2006], Retrieved from the Internet: www. scabusa. org/pdfs_dbupload/00_ARS -FPR_Elias_Final.PDF>; 4 pgs.

Elias, Elias "*Fusarium* Head Blight Research," Annual Progress Report, Grant No. 59-0790-9-033 [online]. U.S. Wheat and Barley Scab Initiative, United Stated Department of Agriculture-Agricultural Research Service, 2000 [retrieved on Apr. 7, 2006]. Retrieved from the Internet:www.scabusa.org/pdfs_dbupload/00PRF_EliasE.PDF>; 4 pgs.

Elias, Elias "*Fusarium* Head Blight Research," Annual Progress Report, Grant No. 59-0790-9-033 [online]. U.S. Wheat and Barley Scab Initiative, United Stated Department of Agriculture-Agricultural Research Service, 1999 [retrieved on Apr. 7, 2006]. Retrieved from the Internet://www.scabusa.org/pdfs_dbupload/FY99_Elias_PR.PDF>; 5 pgs.

Elias, "Development of *Durum* Wheat Resistant to *Fusarium* Head Blight" 2001 National *Fusarium* Head Blight Forum Proceedings, U.S. Wheat & Barley Scab Initiative [online]. Erlanger, KY Dec. 8, 2001 to Dec. 10, 2001, available online [retrieved Apr. 20, 2006]. Retrieved from the Internet:www.scabusa.org/pdfs/forum_01_proc.pdf>; Title page, Publication page, Table of Contents, and 1 pg abstract (13 pgs.).

Elias et al., "Registration of 'Dilse' *durum* wheat" *Crop. Sci.*, May 2004; 44(3):1024.

Elias et al., "Registration of 'Pierce' *durum* wheat" *Crop Sci.*, May 2004;44(3):1025.

Elias et al., "Registration of 'Lebsock' *Durum* Wheat" *Crop Sci.*, Nov.-Dec. 2004;41(6):2007-2008.

Elias et al., "Registration of 'Plaza' *Durum* Wheat" *Crop Sci.*, Nov.-Dec. 2001;41(6):2008.

Elias et al., "Registration of 'Maier' *Durum* Wheat" *Crop Sci.*, 2000 40:1498-1499.

Elias et al., "Registration of 'Belzer' *Durum* Wheat" *Crop Sci.*, 1999;39:881-882.

Elias et al., "Registration of 'Ben' *Durum* Wheat" *Crop Sci.*, 1997;38:895.

Gehlhar et al., "A *Species Cytoplasm Specific* Gene in Euplasmic *Durum* Wheat Does Not Alter Field Performance" *Crop Sci.*, Sep.-Oct. 2005;45(5):1704-1707.

Klindworth et al., "Registration of four *durum* germplasms carrying glutenin allele Glu-D1d on a 1AS.1AL-1DL translocation chromosome" *Crop Sci.*, Mar.-Apr. 2006; 46(2):1002-1003.

Klindworth et al., "Agronomic and quality characteristics of IAS.1AL-1DL translocation lines of *durum* wheat carrying glutenin allele *Glu-D1d*" *Crop Sci.*, Jan-Feb. 2005;45(1):77-84.

Knott, "Sceptre *durum* wheat" *Can. J. Plant Sci.*, 1986;66:407-408.

Kolb et al., "Symposium on Genetic Solutions to *Fusarium* Head Blight in Wheat and Barley: Challenges, Opportunities, and Imperatives, Host Plant Resistant Genes for *Fusarium* Head Blight: Mapping and Manipulation With Molecular Markers" *Crop Sci.*, May-Jun. 2001;41(3):611-619.

Leisle, "Medora *durum* wheat" *Can. J. Plant Sci.*, 1986;66:999-1000.

Liu, "Recent advances in research on wheat scab in China," in *Wheat for more tropical environments: Proceedings of the International Symposium*, Centro Internacional de Mejoramiento de Maiz y Trigo, Mexico, D.F. Mexico Sep. 24, 1984 to Sep. 28, 1984, pp. 174-181.

Manthey et al., "Grass control herbicides can affect *durum* wheat quality" *Proc. National Wheat Industry Research Forum*, 2001;4:Title page, table page, and 51-52 (4 pages).

McMullen et al., "*Fusarium* Head Blight (Scab) of Small Grains" [online]. North Dakota State University, Fargo, ND Dec. 1999 PP-804 [retrieved on Apr. 7, 2006]. Retrieved from the Internet:www.ext.nodak.edu/extpubs/plantsci/smgrains/pp804w.htm#Symptoms>; 6 pgs.

McMullen, "Evaluation of Fungicides for Suppression of *Fusarium* Head Blight," in *Current Research on Fusarium head blight of small grains*, NDSU Research Publication, Fargo, ND 1997 (1 page).

"OSU-OARDC Plant Germplasm Release Guidelines and Practices" Definition of Terms [online]. The Ohio State University, Columbus, OH [retrieved on Jan. 13, 2005]. Retrieved from the Internet:ohioline.osu.edu/sc178/sc178_13.html>; 3 pgs.

Otto et al., "Genetic dissection of a major *Fusarium* head blight QTL in tetraploid wheat" *Plant Mol. Biol.*, Mar. 2002;48(5):625-632.

"Plant Resistance" [online]. North Dakota State University, Fargo, ND [retrieved on Apr. 6, 2006]. Retrieved from the lnternet:www.ndsu.edu/entomology/pri.htm>: 1 pg.

Proceedings From the 3rd Canadian Workshop on *Fusarium* Head Blight/Colloque Canadien Sur La Fusariose, Delta Winnipeg, Winnipeg, Manitoba, Canada, Dec. 9, 2003 to Dec. 12, 2003 (175 pgs.).

Ransom et al., "North Dakota *Durum* Wheat Variety Trial Results for 2004 and Selection Guide" [online]. North Dakota State University, Fargo, ND Dec 2004 A-1067 [retrieved on Apr. 7, 2006]. Retrieved from the Internet:www.ext.nodak.edu/extpubs/plantsci/smgrains/a1067w.htm>; 8 pgs.

Rudd et al., "Host plant resistance genes for *Fusarium* head blight: Sources, mechanisms, and utility in conventional breeding systems" *Crop Sci.*, May-Jun. 2001;41(3):620-627.

Satyavathi et al., "Effects of growth regulators on in vitro plant regeneration in *durum* wheat" *Crop Sci.*,Sep.-Oct.;44(5):1839-1846.

Sayler, "Scab on a rampage: where do we go from here?" *Prairie Grains*, Nov. 1997;(10):14, 19-21, 35, 39.

Sayler, "Scab on a rampage: where do we go from here?" *Prairie Grains*, Nov. 1997;(10):14, 19-21, 35, 39. [retrieved on Mar. 30, 2006]. Retrieved from the Internet:www.smallgrains.org/Springwh/Nov97/Rampage.htm>; 6 pgs.

Stack et al., "*Fusarium* head blight reaction of Langdon *durum-Triticum dicoccoides* chromosome substitution lines" *Crop Sci.*, Mar.-Apr. 2002;42(2):637-642.

Stack et al., "A Visual Scale to Estimate Severity of *Fusarium* Head Blight in Wheat" [online]. North Dakota State University, Fargo, ND Nov. 1998 PP-1095 [retrieved on Apr. 7, 2006]. Retrieved from the Internet:www.ext.nodak.edu/extpubs/plantsci/smgrains/pp1095w.htm>; 2 pgs.

Stack et al., "A Visual Scale to Estimate Severity of *Fusarium* Head Blight in Wheat" *No. Dak. St. Univ. Bull.*, 1995 P-1095, 3 pages.

Stack, "A comparison of inoculum potential of ascospores and conidia of *Gibberella zeae*" *Can. J. Plant Path.*, 1989;11(1):137-142.

Wilcoxson, "Historical review of scab research," in *Proc.* (1st) *Regional Scab Forum*, Publ. Minn. Wheat Res. & Prom. Council, Moorhead, MN 1993, pp. 1-5.

Frohberg et al., "Registration of Spring Wheat Germplasm ND2710 Resistant to *Fusarium* Head Blight," 2004. *Crop Science*. 44:1498-1499.

Oliver et al., "Evaluation of *Fusarium* Head Blight Resistance in Tetraploid Wheat (*Triticum turgidum* L.)," Jan.-Feb. 2008 *Crop Sci* 48:213-222.

* cited by examiner

BREEDING OF *FUSARIUM* RESISTANT TETRAPLOID *DURUM* WHEAT

This application claims the benefit of U.S. Provisional Application Ser. No. 60/577,854, filed 8 Jun. 2004, which is incorporated herein by reference in its entirety.

STATEMENT OF GOVERNMENT RIGHTS

This invention was made with government support under a grant from the United States Department of Agriculture-Agricultural Research Service (USDA-ARS), Grant No. 59-0790-9-033. The U.S. Government has certain rights in this invention.

BACKGROUND OF THE INVENTION

Durum wheat (the tetraploid wheat *Triticum turgidum* L. var. *durum*, synonym *T. durum*) is one of the most important cereal crops in the world. Also known as "hard" wheat or macaroni wheat, it is cultivated in semiarid regions of the world such as North Africa, Mediterranean Europe, the North American Great Plains and the Middle East. Its kernel size, hardness and golden amber color make it most suitable for manufacturing a unique and diverse range of food products. Pasta and couscous are the most common paste products made from durum wheat.

Durum wheat also can be used for making bread, however, bread wheat (the hexaploid wheat *T. aestivum*) is the main source of flour for making bread. Generally bread wheat is not used to manufacture pasta or couscous.

Wheat belongs to the genus *Triticum*, all members of which contain a multiple of the basic haploid set of seven chromosomes ($x=7$). The wheats form an all polyploid series with diploid ($2n=2x=14$), tetraploid ($2n=4x=28$), and hexaploid ($2n=6x=42$) species. Within each species, chromosomes pair in a diploid-like fashion, and the mode of inheritance is disomic.

Cytogenetic, biochemical, morphological and genetic analyses have been used to assess the evolutionary development of the cultivated tetraploid and hexaploid wheat. The designated A-genome is derived from the diploid *T. monococcum* L. (synonyms *T. boeoticum* and *T. urartu*). *T. monococcum* was long considered the A-genome donor. At the wild tetraploid level, *T. dicocoides* (AABB) may have the A-genome from *T. monococcum* and the B-genome of *T. speltoides* (Tausch) Gren. Ex Richter, synonym *Aegilops speltoides*. Common bread wheat, the hexaploid *T. aestivum* (AABBDD) has the A- and B-genomes of a tetraploid *T. turgidum* and the D-genome derived from *T. taushii* (Coss.) Schmal., synonym *Aegilops sqarrosa*. The two species *T. turgidum* L. var. *dicoccoides* and *Aegilops sqaurrosa* are considered the nearest wild progenitors of common bread wheat. *T. dicoccoides* is the only wild member of the wheat group fully interfertile with cultivated *T. turgidum* L var. *durum*.

The tetraploid emmer wheats *T. dicoccum* shrank, *T. dicoccoides*, and *T. turgidum* L var. *durum* also can be crossed directly with hexaploid wheats. The $F_1$ generation may exhibit a high degree of sterility, but seed set can be obtained.

Fusarium head blight (FHB) is caused by the fungus *Fusarium*, typically *F. graminearum* Schwabe (telomorph *Gibberella zea* (Schwein.) Petch) but other causal agents can include *F. culmorum* and *F. avenaceum*. Fusarium head blight is a serious threat to durum wheat. Since 1993, it is estimated that Fusarium head blight has cost over $3 billion in direct and indirect losses in North Dakota (Sayler, Scab on rampage: where do we go from here? Prairie Grains, November/December, issue 10 pp 14, 19-21, 35 and 39 (1997)). Fusarium head blight not only reduces yield but also reduces the quality of the end products of durum wheat (Dexter et al., Cereal Chem., 74:519 (1997)). The fungus is also associated with mycotoxins, particularly trichothecene deoxynivalenol (DON vomitoxin), that are hazardous to humans and other animals.

There is a continuous decline in harvested durum acreage and production in North Dakota because of Fusarium head blight. The harvested acreage in North Dakota in 2001 was 2.25 million acres. This acreage is 22% less than the year 2000 (State of North Dakota, Agriculture Statistics). In 2001 North Dakota produced 60.75 million bushels of durum wheat, which was a 22% decrease in production as compared to production in the year 2000 (National Agriculture Statistics, 2001). The decline in harvested acreage and durum production in North Dakota is disastrous to the farm economy and has direct impact on the national pasta industry. In addition, the international export market is also greatly affected since North Dakota on average produces 75% of the durum in the United States.

Fungicides can be used to improve yield and other agronomic traits but the level of improvement is below the margin of the economic return (McMullen, Evaluation of fungicides for suppression of Fusarium head blight. in Current research on Fusarium head blight of small grains, November (1997) NDSU research publication, Fargo, N.Dak. (1997)). Although fungicides may reduce Fusarium head blight, the use of genetic resistance is the most environmentally safe and economical way to control the disease. Durum wheat with appropriate combinations of resistant genes could effectively control the disease. Accordingly, what is needed is the development of wheat, particularly durum wheat, that is genetically resistant to *Fusarium*.

SUMMARY OF THE INVENTION

The invention provides *Fusarium* resistant tetraploid wheat as well as methods for making and using such wheat. A preferred embodiment of the method of producing *Fusarium* resistant tetraploid wheat includes crossing *Fusarium* resistant hexaploid wheat with a tetraploid wheat to produce $F_1$ progeny, backcrossing the $F_1$ progeny with a tetraploid wheat to produce backcrossed $F_1$ ($BC_1F_1$) progeny, and selfing the backcrossed $F_1$ ($BC_1F_1$) progeny to produce backcrossed progeny ($BC_1F_2$) that include the *Fusarium* resistant tetraploid wheat.

Seeds and other plant parts of *Fusarium* resistant tetraploid wheat, such as a leaf, stem, root, embryo, meristematic tissue, callus tissue, germplasm, gametophyte, saprophyte, pollen or microspore, are also provided by the invention. Progeny of *Fusarium* resistant tetraploid wheat plants, including progeny of crosses and backcrosses utilizing *Fusarium* resistant tetraploid wheat, are also included in the invention.

DETAILED DESCRIPTION OF ILLUSTRATIVE EMBODIMENTS

Figure 1:
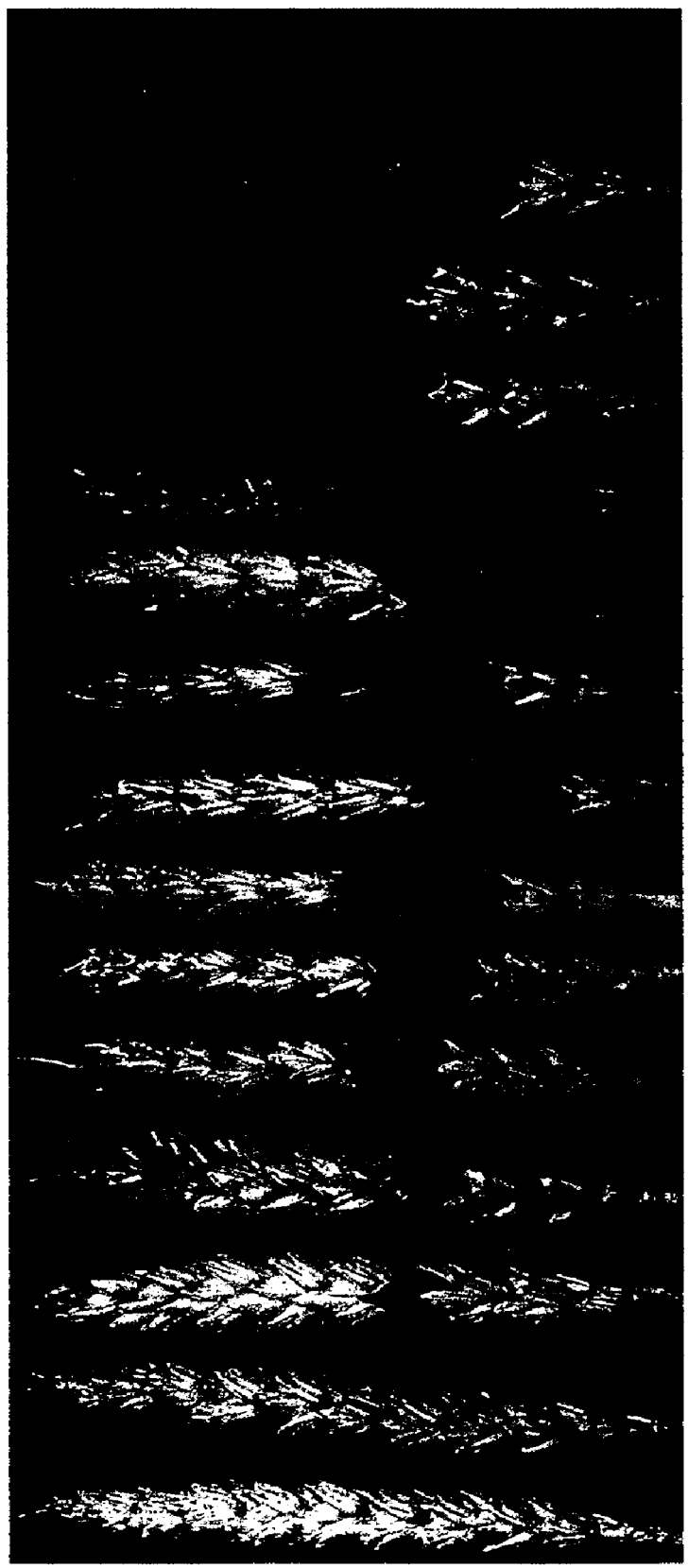
FIG. 1 is a gray scale for determining Fusarium head blight (FHB) disease severity (% disease severity is indicated on the x-axis) (Stack and McMullen, A visual scale to estimate severity of Fusarium head blight in wheat. No. Dak. St. Univ. Bull. P-1095 (1995)).

The present invention is based on the discovery that resistance to Fusarium head blight (FHB) (also referred to herein as "Fusarium resistance" or "FHB resistance") can be transferred from known Fusarium resistant hexaploid wheat to tetraploid wheat through use of the method of the invention. Accordingly, the invention also provides Fusarium resistant tetraploid wheat, and products thereof, that will help to provide good quality wheat for the future. The Fusarium resistant wheat produced according to the method is produced through use of basic plant breeding and is therefore not a genetically modified organism.

The term "wheat" as used herein includes generally any plant of the wheat genus (Triticum) including wheat species, varieties, subvarieties, hybrids, cultivars, lines, strains and the like.

Hexaploid Wheat

The method for producing a Fusarium resistant tetraploid wheat involves the transfer of Fursarium resistance from a hexaploid Fusarium resistant wheat to a tetraploid wheat. Many types of Fusarium resistant hexaploid wheat are known. Examples of Fusarium resistant hexaploid wheat varieties include, but are not limited to, Sumai 3 wheat, Ning 7840 wheat, Frontana wheat, Nobeokabouza wheat, 2375 wheat, Ernie wheat, Freedom wheat and Wnagshuibai wheat (Rudd et al., Crop Sci., 41:620 (2001)). Many of these types of Fusarium resistant hexaploid wheat have molecular markers that are associated with the Fusarium resistance, such as Xgwm2, Qjhs.ndsu-3BS and Xgwm533 (Rudd et al., Crop Sci., 41:620 (2001) and Anderson et al., Theor. Apl. Genet., 102:1161 (2001)). These types of Fusarium resistant hexaploid wheat, and others, may be used within the method of the invention to produce Fusarium resistant tetraploid wheat.

The Fusarium resistant hexaploid wheat, Sumai 3, is probably the most widely used wheat from which Fusarium resistance is obtained in the world. It has been used in Chinese breeding programs for at least 20 years (Liu, Recent advances in research on wheat scab in China. p. 174-181, in Wheat for more tropical environments. CIMMYT (Centro Internacional de Mejoramiento de Maiz y Trigo), Mexico, D.F. Mexico (1984)) and since introduction into the USA, it has been used by winter and spring wheat breeders (Wilcoxson, Historical review of scab research, p. 1-5, in Proc. (1$^{st}$) Regional Scab Forum, Moorhead, Minn. Publ. Minn. Wheat Res. & Prom Council, Red Lake Falls, Minn. (1993)). The FHB resistance in Sumai 3 is heritable, stable and consistent across environments.

The Fusarium resistant hexaploid spring wheat, Wnagshuibai, has also been used by wheat breeders in the USA, but has not been as widely used as Sumai 3. The FHB resistance in Wnagshuibai is also heritable, stable and consistent across environments.

While Sumai 3 has been successfully used by hexaploid wheat breeders as a source of Fusarium resistance, tetraploid durum wheat breeders have had no success in using it. This lack of success initially led breeders to believe that the resistance genes from Sumai 3 might be on the D-genome of hexaploid wheat and would therefore not recombine with tetraploid durum wheat where the D-genome is absent (the durum genome is AABB). However, the resistance genes from Sumai 3 have been mapped on the A-genome and the B-genome (Kolb et al., Crop Sci., 41:611 (2001)). It is now believed that the genetic background of the elite durum germplasm may be surpressing the Sumai 3 resistance. Accordingly, it was surprising when resistance from hexaploid Sumai 3 wheat and hexaploid Wangshuibai wheat was successfully transferred to tetraploid elite North Dakota durum wheat germplasm using the method of the invention.

Fusarium Resistance

Fusarium or FHB "resistance" refers to the ability of wheat to resist infection by Fusarium. There are a number of ways to measure resistance to FHB, which include measuring resistance to initial infection, resistance to spreading (Type II resistance), resistance to kernel infection, tolerance and toxin accumulation/degradation. Preferably, FHB resistance is evaluated using an assay for "Type II" resistance, where an infection is introduced into the middle of a stalk and the plant is examined for spreading up or down the stalk. In a resistant plant, the infection will remain localized, perhaps infecting only one floweret or spikelet. Most breeding programs target "Type II" resistance, i.e., resistance to spread of infection within the spike of a plant.

Figure 2:
FIG. 2 is a gray scale version of color photographs showing FHB severity (% disease severity is indicated on the x-axis) (Stack and McMullen, A visual scale to estimate severity of Fusarium head blight in wheat. No. Dak. St. Univ. Bull. P-1095 (1995)).

FHB resistance can be evaluated, for example, by examining the plant for disease after exposure to a Fusarium inoculum. Wheat can be planted and inoculated with Fusarium according to methods described herein and known in the art (e.g., Stack, Can. J. Plant Path., 11:137 (1989)). The wheat is then inspected to determine the level (e.g., spreading) of Fusarium infection (disease severity) produced on the wheat. A visual scale, as shown in FIG. 1 and FIG. 2, and as described in the art (e.g., Stack and McMullen, A visual scale to estimate severity of Fusarium head blight in wheat. No. Dak. St. Univ. Bull. P-1095 (1995)) and in Example I below, is commonly used to assess resistance to Fusarium. Fusarium resistance can be tested under a variety of conditions, such as in a nursery setting and/or in a field setting.

Fusarium resistance and disease severity are, of course, inversely related. A high "% disease severity" value indicates that a wheat exhibits low resistance to Fusarium while a low "% disease severity" value indicates that a wheat exhibits high resistance to Fusarium infection.

Hexaploid wheat is generally resistant to Fusarium. Disease severity typically exhibited by hexaploid wheat ranges from 7% to 20%. Disease severity typically observed in non-Fusarium resistant tetraploid wheat ranges from 35% to 100%.

Preferably the level of disease severity of the Fusarium resistant tetraploid wheat of the invention is less than 32%, more preferably the level of disease severity of the Fusarium resistant tetraploid wheat is less than 20%, most preferably the level of disease severity of the Fusarium resistant tetraploid wheat is less than 10%. Preferably the level of disease severity of the Fusarium resistant tetraploid wheat is between 7% and 30%. More preferably the level of disease severity of the Fusarium resistant tetraploid wheat is between 7% and 20%. Most preferably the level of disease severity of the Fusarium resistant tetraploid wheat is between 7% and 10%.

Preferably a progeny tetraploid wheat to which Fusarium resistance is transferred through crossing with a Fusarium resistant hexaploid wheat exhibits greater Fusarium resistance than the parent tetraploid wheat.

The presence or level of Fusarium resistance can also be assessed through use of molecular markers that are linked to Fusarium resistance. For example, the microsatellite locus Xgwm2 is tightly linked to Fusarium resistance (Otto et al., Plant Molecular Biology, 48:625 (2002)). Other examples of molecular markers that are associated with Fusarium resistance include a major quantitative trait loci that is designated Qfhs.ndsu-3BS, and a simple sequence repeat marker that is designated Xgwm533. Accordingly, wheat can be additionally assessed for Fusarium resistance based on the presence of a molecular marker within the screened wheat. Additional markers that are associated with Fusarium resistance can also be used to screen wheat for Fusarium resistance.

Tetraploid Wheat

Fusarium resistance is transferred according to the invention from Fusarium resistant hexaploid wheat to tetraploid wheat. Tetraploid wheat includes, but is not limited to, T. dicoccum shrank, T. dicoccoides, and T. turgidum L var. durum (durum wheat) and T. turgidum polonicum (Kamut).

Preferably, the tetraploid wheat is a durum wheat. Examples of durum wheat varieties include Belzer, Ben, Dilse, Lebsock, Maier, Mountrail, Munich, Pierce, Plaza, Sceptre, Medora, D88096, D88816, D88090 and D88690. Preferably the tetraploid wheat to which *Fusarium* resistance is transferred is durum wheat.

Some durum wheat already exhibit an increased level of *Fusarium* resistance. For example, the newly released cultivars: Lebsock (Elias et al., Crop Sci., 41:2007 (2001)), Plaza (Elias et al., Crop Sci., 41:2008 (2001)), Maier (Elias and Miller, Crop Sci., 40:1498 (2000)), Belzer (Elias et al., Crop Sci., 39:881 (1999)) and Ben (Elias and Miller, Crop Sci., 38:895 (1998)) have less disease severity and deoxynivalenol (DON) levels than the older cultivars, Renville (Cantrell et al., Crop Sci., 29:1329 (1989)) and Monroe (Cantrell et al., Crop Sci., 26:200 (1986)). However, the level of resistance in these cultivars is still much lower than that found in hexaploid wheat germplasm. Observed disease severities were within a range of 30% to 60%. It has been reported that the durum Langdon *dicoccoides* 3A substitution line [LDN(DIC-3A)] was less susceptible to FHB, 12.5% to 29.9%, than all the other substitution lines (Stack et al., Crop Sci., 42:637 (2002)). In comparison with the resistance of Sumai 3, LDN (DIC-3A) is characterized as moderately resistant, with a mean disease severity of 19.8%. A microsatellite locus, Xgwm2, is tightly linked to this resistance (Otto et al., Plant Molecular Biology, 48:625 (2002)) and is being used in the durum breeding program at North Dakota State University (NDSU).

Plant Breeding

The method for producing *Fusarium* resistant tetraploid wheat includes crossing hexaploid *Fusarium* resistant wheat with tetraploid wheat to produce $F_1$ progeny, backcrossing the $F_1$ progeny with tetraploid wheat to produce a backcrossed $F_1$ ($BC_1F_1$) progeny, and selfing the backcrossed $F_1$ progeny to produce backcrossed progeny ($BC_1F_2$) that include members that are resistant to *Fusarium*.

A single cross is a cross between two parents, for example between Sumai 3 (hexaploid) and Sceptre (tetraploid) which is labeled as Sumai 3/Sceptre. Making crosses requires emasculating the female flower and later pollinating it with pollen from the male flower. Forceps are used for emasculation to remove the anthers from the female flower (female parent). The emasculated female flower is covered with glassine bags to avoid out-crossing. Four to five days later when the flower is mature enough to be receptive, pollen is transferred from the male flower. Thirty days later hybrid seed is harvested and planted to produce $F_1$ progenies.

A "backcross," as that term is used herein, is a cross between (a) an $F_1$ progeny and (b) one of its parents or a variety with one or more similar features of a parent (the latter being sometimes known as a "top cross"). In the present method, the purpose of the backcross is to reconstitute the tetraploid background. For example, after a hexaploid wheat (e.g., Sumai 3) is crossed with a tetraploid wheat (e.g., Sceptre), $F_1$ progeny can be crossed to another tetraploid wheat as a backcross. Sumai 3 can, for example, be crossed to Sceptre, and the resulting $F_1$ (Sumai 3/Sceptre) can be crossed to a tetraploid line D88816. This backcross is labeled as Sumai 3/Sceptre//D88816, with D88816 being used to reconstitute the tetraploid background.

Advantageously, *Fusarium* resistant tetraploid wheat (for example, the experimental durum lines described in Example I) can be crossed with the germplasm of any tetraploid wheat of interest to produce an FHB resistant plant with additional desired traits. These traits exhibited by the plant can be observable in the plant's phenotype and/or genotype. The progeny of such crosses may exhibit traits such as improved yield, pasta quality and/or robustness. By crossing *Fursarium* resistant tetraploid lines with other, agronomically acceptable lines, germplasm can be developed that is both agronomically acceptable and disease resistant. The present invention thus encompasses the use of *Fusarium* resistant tetraploid wheat as a parent in crosses with other tetraploid wheat, as well as the *Fusarium* resistant progeny of such crosses.

Optionally, members of the backcrossed progeny ($BC_1F_2$) are then selected using selection criteria that can include, but are not limited to, plant features such as plant type, fertility, plant height, head type, maturity, kernel type, and the like. Selected members of the backcrossed progeny ($BC_1F_2$) are then selfed to produce additional ($BC_1F_3$) progeny, which are selected using selection criteria and selfed to produce ($BC_1F_4$) progeny. This process is continued until tetraploid wheat is produced that has increased *Fusarium* resistance, and other plant features that were selected. This process may be repeated until tetraploid wheat is produced having the selected plant features. In some examples, selfed progeny are produced by performing one to seven selfings, one to ten selfings, one to twenty selfings, and single integer selfings thereof. Examples of such single integer selfings include ($BC_1F_6$), ($BC_1F_7$), ($BC_1F_8$), ($BC_1F_9$), ($BC_1F_{10}$), ($BC_1F_{11}$), progeny and so on.

In a preferred embodiment of the method of producing *Fusarium* resistant tetraploid wheat, the $F_2$ population is large in number (e.g., more than 2000 members, preferably more than 3,000 members, most preferably more than 4,000 members) and a relatively large number of those members (e.g., over 100, preferably over 200) are selected for selfing. Families $F_3$, $F_4$, $F_5$, $F_6$, $F_7$, $F_8$, $F_9$, and so on, are also large compared to standard breeding protocols. The large size of the families increases the probability of a recovery of a line that has *Fusarium* resistance. Selection within a family, even if the family is 98% genetically identical, surprisingly yields plants with genetic differences. Some of these selected plants exhibited *Fusarium* resistance. Most breeders do not select within $F_5$ families because of the little genetic diversity present in these families, as they have reached 96.875% homozygosity. However, as described herein in Example I, the little genetic variability present in the $BC_1F_5$ generation was productively explored.

As shown in Example I, tetraploid wheat produced through transfer of *Fusarium* resistance from hexaploid wheat to the tetraploid wheat according to this method exhibit a *Fusarium* disease severity of about 7% to about 16% in greenhouse testing and about 12% to about 32% in field testing.

The present invention is illustrated by the following examples. It is to be understood that the particular examples, materials, amounts, and procedures are to be interpreted broadly in accordance with the scope and spirit of the invention as set forth herein.

EXAMPLES

Example I

Preparation of FHB Resistant Tetraploid Wheat

Summary

Tetraploid wheat that was not resistant to *Fusarium* was crossed with *Fusarium* resistant hexaploid wheat. The progeny were then backcrossed with tetraploid wheat to produce backcrossed $F_1$ ($BC_1F_1$) progeny. The backcrossed F1 progeny were then selfed to produce backcrossed progeny ($BC_1F_2$) that include the *Fusarium* resistant tetraploid wheat.

Materials

Sceptre and Medora durum wheat were developed by the Department of Plant Science and Plant Pathology at the University of Saskatchewan and were released on 5 Jul. 1985 and May, 1982, respectively. Sceptre and Medora exhibit high yield and quality but do not exhibit *Fusarium* resistance. A complete description of Sceptre has been published (Knott, Can. J. Plant Sci., 66:407 (1986)). A complete description of Medora has also been published (Leisle, Can. J. Plant Sci., 66:999 (1986)).

Ben durum wheat was developed by the North Dakota Agricultural Experiment Station in cooperation with USDA-ARS and released in March of 1996. Ben was registered and was protected under the U.S. Plant Variety Protection Act for Foundation, Registered, and Certified seed classes (PVP Certificate no. 9700089) (Elias et al., Crop Science, 38:895 (1998)). Ben durum wheat also does not exhibit *Fusarium* resistance.

The durum experimental lines D88096, D88816, D88090 and D88690 were developed by the Durum Wheat Breeding Program at North Dakota State University for possible release as varieties. These wheat varieties also do not exhibit *Fusarium* resistance.

Methods

The tetraploid wheat varieties Sceptre, Medora, and Ben, and the tetraploid experimental lines D88096, D88816, D88090 and D88690 were crossed and backcrossed with the *Fusarium* resistant hexaploid wheat, Sumai 3 or Wnagshuibai, to produce FHB resistant tetraploid durum wheat.

Specifically, Sumai 3 was crossed to Sceptre (Sumai 3/Sceptre) and Medora (Sumai 3/Medora). Wnagshuibai was crossed to Ben (Wnagshuibai/Ben).

The $F_1$ resulting from the Sumai 3/Sceptre cross was backcrossed to the four durum experimental lines, D88096, D88816, D88090 and D88690, to generate four different backcrosses $F_1$ ($BC_1F_1$) Sumai 3/Sceptre//D88096, Sumai 3/Sceptre//D88816, Sumai 3/Sceptre//D88090, and Sumai 3/Sceptre//D88690.

The $F_1$ resulting from the Sumai 3/Medora cross was backcrossed to Medora to generate backcross $F_1$ ($BC_1F_1$) Medora//Sumai 3/Medora.

The $F_1$ resulting from the Wnagshuibai/Ben cross was backcrossed to Ben to generate backcross $F_1$ ($BC_1F_1$) Wnagshuibai/Ben//Ben.

The purpose of the backcross is to reconstitute the tetraploid background. All $BC_1F_1$ wheat were selfed to produce $BC_1F_2$ progenies.

The $BC_1F_1$ progenies were planted in a field and single head (spike) selections were made from the $BC_1F_2$ generation for durum plant type, fertility, plant height, head type, maturity, kernel type, and other agronomic traits. $BC_1F_3$ head rows were made following these selections. At the $BC_1F_3$, further selections were made from the $BC_1F_3$ generation for the same traits described earlier. First selection was practiced among head rows then within each selected head row the best two plants were selected and planted as sister head rows in the next generation. The $BC_1F_4$ head rows were made from these selections. A similar selection procedure to the $BC_1F_3$ generation was practiced to develop the $BC_1F_5$ generation.

The $BC_1F_5$ generations were planted as head hill plots (20 seed/hill) in a field Fusarium head blight nursery at Prosper, N.Dak. for FHB evaluation and selection.

Corn colonized with *F. graminearum* (grain spawn) was used as a source of inoculum in the nursery. The grain spawn was spread onto the ground by hand at a rate of 40 grams/$meter^2$. The first spawn was spread when the durum wheat was about two weeks from flowering. Additional fresh spawn was spread when needed. The nursery was equipped with a misting system to keep humidity at optimum level for disease development.

First selection was practiced for FHB resistance among head hill plots. Then, within each selected hill plot, the best six plants were selected and planted as sister head rows ($BC_1F_6$) in the next generation.

The $BC_1F_6$ generations were planted as head rows in a Fusarium head blight nursery at the Academy of Agricultural Sciences, Plant Protection Institute Shanghai, China, (AASP-PIS). Twenty kernels from each accession were planted in single 1.5 meter long rows. Entries were assigned to experimental units using a modified augmented block design. Two to three weeks prior to flowering, rice and wheat kernels infected with *F. graminearum* were spread by hand onto the ground to create an artificial epidemic. The nursery was equipped with a misting system to keep humidity at the optimum level for disease development. Resistant rows were selected and then $BC_1F_7$ heads from the selected head rows were selected, threshed, and shipped back to North Dakota State University.

The $BC_1F_7$ heads were planted as head rows in the nursery at North Dakota State University for FHB evaluations. Methods of inoculum preparation and inoculation in the nursery that were used are known (Stack, Can. J. Plant Path., 11:137 (1989)). The single spikelet injection method was used in which the inoculum is injected into a single spikelet near the middle of the spike near anthesis. Plants were misted periodically to maintain high humidity for disease development. Plants were rated for Type II disease severity 3 to 3.5 weeks after inoculation using a known scale as described herein (Stack and McMullen, A visual scale to estimate severity of FHB in wheat. No. Dak. St. Univ. Bull. P-1095 (1995)). Mean Type II disease severity of progenies from these crosses are presented in Table 2. Selected lines that are in Table 2 were planted as a randomized complete design trial with four replicates in the field in 2002 for evaluations relying on natural epidemic.

The trial was also planted in the field Fusarium head blight screening nursery at Prosper, N.Dak. Environmental conditions in 2002 were favorable for inducing a severe natural FHB epidemic. The natural epidemic provided good data for the trial that was not in the screening nursery. Data from this trial is presented in Table 3. Fusarium head blight Type II disease severity ratings of these lines in the trial ranged from 13% to 31.5%.

The resulting experimental durum lines, which represent *Fusarium* resistant tetraploid wheat, are indicated by the following identifiers: D011511, D011502, D011513, D011509, D011516, D011522, D011507, D011501, D011519, D011524, D011510, D011506, D011512, D011503, D011525, D011517, D011515, D011508, D011518, D011521, D011514, D011523 and D011520 as described herein.

Mitotic Chromosome Observation

All lines generated from the crosses were checked for chromosome number to insure their ploidy level and check for any abnormalities such as monosomics or chromosome additions. Seeds of the durum wheat lines were germinated on wet filter paper in a petri-dish at 25° C. Roots that were 2-3 cm long were collected and treated in ice water for 20 hours. The roots were then fixed in a solution of 3:1 (95% alcohol:glacial acetic acid). The roots were stained with 2% acetocarmine at room temperature for 1-2 hours before chromosome preparation. Mitotic chromosomes were prepared following known procedures (Cai and Liu, Theor. Appl. Genet., 77:81 (1989)). Mitotic chromosomes in each of the durum lines were counted under an Olympus microscope. All lines were found to have 14 pairs of chromosomes without any abnormalities indicating that they are tetraploid wheat.

Molecular Markers for FHB Resistance

Identification of DNA markers associated with FHB resistance is thought to be a useful tool for wheat breeders working on developing FHB resistant wheat germplasm. A considerable number of mapping studies have been conducted on the Type II resistance of Sumai 3 and its derivatives. A major quantitative trait loci (QTL) was identified in Sumai 3 and designated as Qjhs.ndsu-3BS that is widely used by wheat breeders in the United States. A SSR (Simple Sequence Repeats) marker Xgwm533 that explains 41.6% of the variation of FHB resistance associated with this QTL has been identified (Anderson et al., Theor. Apl. Genet., 102:1161 (2001)). Many breeding programs are using the Xgwm533 marker to check the presence of this QTL in their germplasm. The Xgwm533 was also used to check the presence of the Sumai 3 QTL in the progenies of the hexaploid by tetraploid crosses.

For DNA extraction, a Flinders Technology Associates (FTA) plant purification protocol was used. Leaf tissue was collected at the three leaf stage and smashed onto the FTA cards. Cell membranes and organelles in the leaf tissue were lysed and DNA becomes entrapped in the fibers of the FTA matrix due to being smashed onto the FTA cards. A 2.0 mm punch from within the middle of the smashed leaf stain was removed using a 2.0 mm Harris Micro Punch tool and transferred to an appropriate PCR amplification tube. Each punch was washed twice with 200 µL of FTA reagent followed by an equal number of washings with TE 10 mM Tris-Hcl pH 8.0; 0.1 mM EDTA ph 8.0. The punch was then dried at room temperature for 3 hours and then used for PCR amplification. The presence or absence of the marker in the lines is reported in Table 2 and Table 3.

TABLE 2

*Fusarium* head blight percent mean disease severity and presence (+) or absence (−) of the marker Xgwm533 of durum lines evaluated in a greenhouse in the Spring of 2000

| Entry | Label | Pedigree | % Disease Severity | Xgwm533 |
|---|---|---|---|---|
| 28 | D011511 | Sumai 3/Sceptre//D88816 | 7.0 | + |
| 29 | D011502 | Sumai 3/Sceptre//D88816 | 7.0 | − |
| 69 | D011513 | Wangshubai/Ben//Ben | 7.0 | + |
| 20 | D011509 | Sumai 3/Sceptre//D88690 | 7.4 | − |
| 80 | D011516 | Wangshubai/Ben//Ben | 8.0 | − |
| 95 | D011522 | Medora//Sumai 3/Medora | 8.1 | − |
| 7 | D011507 | Sumai 3/Sceptre//Sceptre | 8.3 | − |
| 13 | D011501 | Sumai 3/Sceptre//D88096 | 8.4 | − |
| 88 | D011519 | Wangshubai/Ben//Ben | 8.4 | + |
| 113 | D011524 | Sumai 3/Sceptre//Sceptre | 8.5 | − |
| 25 | D011510 | Sumai 3/Sceptre//D88816 | 9.0 | − |
| 114 | D011506 | Sumai 3/Sceptre//D88090 | 9.2 | + |
| 66 | D011512 | Sceptre/Sumai 3//Sceptre | 9.2 | − |
| 30 | D011503 | Sumai 3/Sceptre//D88816 | 9.5 | − |
| 117 | D011525 | Sumai 3/Sceptre//D88816 | 9.7 | + |
| 97 | D011517 | Wangshubai/Ben//Ben | 10.0 | + |
| 80 | D011515 | Wangshubai/Ben//Ben | 10.9 | + |
| 15 | D011508 | Sumai 3/Sceptre//D88096 | 11.9 | − |
| 86 | D011518 | Wangshubai/Ben//Ben | 13.0 | − |
| 94 | D011521 | Medora//Sumai 3/Medora | 13.0 | − |
| 75 | D011514 | Wangshubai/Ben//Ben | 13.2 | + |
| 100 | D011523 | Medora//Sumai 3/Medora | 13.5 | + |
| 91 | D011520 | Wangshubai/Ben//Ben | 15.8 | − |
| 170 | D91103 | Mod. Res. Check | 24.6 | |
| 171 | D88541 | Susceptible Check | 60.6 | |
| LSD (0.05) | | | 18.3 | |

*As shown in FIG. 1 and 2, a smaller % disease severity value indicates greater resistance to *Fusarium* infection.

TABLE 3

Mean days to heading (DTHD), height, *Fusarium* head blight disease severity, and presence (+) or absence (−) of the marker Xgwm533 of lines tested in a 2002 Prosper, North Dakota field test.

| Entry | Label | Pedigree | DTHD | Height cm | % Disease Severity | Xgwm533 |
|---|---|---|---|---|---|---|
| 25 | D011525 | Sumai 3/Sceptre//D88816 | 52.3 | 99.0 | 11.7 | + |
| 11 | D011511 | Sumai 3/Sceptre//D88816 | 53.0 | 96.5 | 13.5 | + |
| 6 | D011506 | Sumai 3/Sceptre//D88090 | 52.3 | 106.0 | 16.2 | + |
| 9 | D011509 | Sumai 3/Sceptre//D88690 | 52.5 | 102.8 | 16.2 | − |
| 12 | D011512 | Sceptre/Sumai 3//Sceptre | 50.3 | 101.3 | 18.0 | − |
| 10 | D011510 | Sumai 3/Sceptre//D88816 | 52.5 | 96.5 | 20.7 | − |
| 17 | D011517 | Wangshubai/Ben//Ben | 50.8 | 103.3 | 22.5 | + |
| 8 | D011508 | Sumai 3/Sceptre//D88096 | 50.0 | 93.8 | 25.2 | − |
| 29 | Belzer | Mod. Res. Check | 53.0 | 96.0 | 25.2 | |
| 21 | D011521 | Medora//Sumai 3/Medora | 49.5 | 97.0 | 25.2 | − |
| 14 | D011514 | Wangshubai/Ben//Ben | 50.8 | 103.3 | 25.2 | + |
| 20 | D011520 | Wangshubai/Ben//Ben | 50.8 | 106.5 | 25.2 | − |
| 24 | D011524 | Sumai 3/Sceptre//Sceptre | 54.3 | 87.3 | 27.0 | − |

TABLE 3-continued

Mean days to heading (DTHD), height, *Fusarium* head blight disease severity, and presence (+) or absence (−) of the marker Xgwm533 of lines tested in a 2002 Prosper, North Dakota field test.

| Entry | Label | Pedigree | DTHD | Height cm | % Disease Severity | Xgwm533 |
|---|---|---|---|---|---|---|
| 7 | D011507 | Sumai 3/Sceptre//Sceptre | 53.0 | 89.5 | 27.0 | − |
| 1 | D011501 | Sumai 3/Sceptre//D88096 | 51.3 | 95.0 | 27.0 | − |
| 23 | D011523 | Medora//Sumai 3/Medora | 49.8 | 95.8 | 27.0 | + |
| 13 | D011513 | Wangshubai/Ben//Ben | 49.8 | 97.0 | 27.0 | + |
| 19 | D011519 | Wangshubai/Ben//Ben | 48.3 | 106.5 | 27.0 | + |
| 18 | D011518 | Wangshubai/Ben//Ben | 47.8 | 107.3 | 27.0 | − |
| 31 | Maier | Mod. Susceptible Check | 52.0 | 88.3 | 29.7 | − |
| 15 | D011515 | Wangshubai/Ben//Ben | 49.5 | 96.0 | 29.7 | + |
| 16 | D011516 | Wangshubai/Ben//Ben | 47.5 | 99.5 | 29.7 | − |
| 30 | D91103 | Mod. Res. Check | 51.8 | 100.8 | 29.7 | − |
| 22 | D011522 | Medora//Sumai 3/Medora | 48.5 | 103.3 | 29.7 | − |
| 2 | D011502 | Sumai 3/Sceptre//D88816 | 50.5 | 88.5 | 31.5 | − |
| 3 | D011503 | Sumai 3/Sceptre//D88816 | 51.3 | 90.0 | 31.5 | − |
| 28 | Rugby | Mod. Susceptible Check | 51.3 | 100.3 | 36.0 | − |
| LSD, (0.05) | | | 1.2 | 5.5 | 1.0 | |
| CV, % | | | 1.7 | 4.0 | 25.5 | |

*As shown in FIG. 1 and 2, a smaller % disease severity value indicates greater resistance to *Fusarium* infection.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method for making a *Fusarium* resistant tetraploid (AABB) durum wheat comprising:
   crossing a hexaploid *Fusarium* resistant wheat with a tetraploid (AABB) durum wheat to produce an $F_1$ progeny;
   backcrossing the $F_1$ progeny with a tetraploid (AABB) durum wheat to produce a backcrossed $F_1$ ($BC_1F_1$) progeny;
   repeatedly selfing the backcrossed progeny for at least five generations without additional backcrossing to produce a backcrossed $F_n$ progeny ($BC_1F_n$), wherein n>5 and the genetic variability within the $F_n$ generation is 3.125% or less; and
   selecting a *Fusarium* resistant tetraploid (AABB) durum wheat from the $F_n$ generation.

2. The method of claim 1, wherein the backcrossed $F_1$ ($BC_1F_1$) progeny for selfing further possess at least one desired trait selected from the group consisting of plant type, fertility, plant height, head type, kernel type, and maturity.

3. The method of claim 1, wherein the hexaploid *Fusarium* resistant wheat comprises a wheat variety selected from the group consisting of Sumai 3, Wnagshuibai, Ning 7840, Frontana, Nobeokabouza, 2375, Ernie and Freedom.

4. The method of claim 1, wherein the tetraploid durum wheat comprises a wheat selected from the group consisting of Sceptre, Medora, Ben, Munich, Belzer, Mountrail, Maier, Lebsock, Plaza, Pierce, and Dilse.

5. The method of claim 1, wherein *Fusarium* resistant tetraploid (AABB) durum wheat exhibits a mean disease severity in a Type II infection field test assay of less than 32%.

6. The method of claim 1, wherein *Fusarium* resistant tetraploid (AABB) durum wheat exhibits a mean disease severity in a Type II infection greenhouse assay of less than 16%.

7. A *Fusarium* resistant tetraploid (AABB) durum wheat produced by the process of:
   crossing a hexaploid *Fusarium* resistant wheat with a tetraploid (AABB) durum wheat to produce an $F_1$ progeny;
   backcrossing the $F_1$ progeny with a tetraploid (AABB) durum wheat to produce a backcrossed $F_1$ ($BC_1F_1$) progeny;
   repeatedly selfing the backcrossed progeny for at least five generations without additional backcrossing to produce a backcrossed $F_n$ progeny ($BC_1F_n$) wherein n>5 and the genetic variability within the $F_n$ generation is 3.125% or less; and
   selecting a *Fusarium* resistant tetraploid (AABB) durum wheat from the $F_n$ generation to yield the *Fusarium* resistant tetraploid (AABB) durum wheat.

8. The *Fusarium* resistant tetraploid (AABB) durum wheat of claim 7 which exhibits a mean disease severity in a Type II infection field test assay of less than 32%.

9. The *Fusarium* resistant tetraploid (AABB) durum wheat of claim 7 which exhibits a mean disease severity in a Type II infection greenhouse assay of less than 16%.

10. A method for making a *Fusarium* resistant tetraploid (AABB) durum wheat, said method comprising:

crossing the *Fusarium* resistant tetraploid (AABB) durum wheat according to claim 7 with another different tetraploid (AABB) durum wheat exhibiting at least one desired trait, to yield a *Fusarium* resistant tetraploid (AABB) durum wheat exhibiting the desired trait.

11. The method of claim 10, wherein the *Fusarium* resistant tetraploid (AABB) durum wheat exhibits a mean disease severity in a Type II infection field test assay of less than 32%.

12. The method of claim 10, wherein the *Fursarium* resistant tetraploid (AABB) durum wheat exhibits a mean disease severity in a Type II infection greenhouse assay of less than 16%.

* * * * *

UNITED STATES PATENT AND TRADEMARK OFFICE
CERTIFICATE OF CORRECTION

PATENT NO.       : 7,652,204 B2                                              Page 1 of 1
APPLICATION NO.  : 11/071272
DATED            : January 26, 2010
INVENTOR(S)      : Elias M Elias It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 637 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO.         : 7,652,204 B2
APPLICATION NO.    : 11/071272
DATED              : January 26, 2010
INVENTOR(S)        : Elias M. Elias It is certified that error appears in the above-identified patent and that said Letters Patent is hereby corrected as shown below:

Column 3, Line 16
Delete "Fursarium" and insert --Fusarium--

Column 5, Line 67
Delete "Fursarium" and insert --Fusarium--

Column 14, Line 4 (Claim 12)
Delete "Fursarium" and insert --Fusarium--

Signed and Sealed this
Twenty-fifth Day of January, 2011

David J. Kappos
*Director of the United States Patent and Trademark Office*